United States Patent [19]

Hillman et al.

[11] Patent Number: 5,861,496
[45] Date of Patent: Jan. 19, 1999

[54] HUMAN SQUALENE EPOXIDASE

[75] Inventors: Jennifer L. Hillman, San Jose; Phillip R. Hawkins, Mountain View, both of Calif.

[73] Assignee: Incyte Pharmaceuticals, Inc., Palo Alto, Calif.

[21] Appl. No.: 745,934

[22] Filed: Nov. 7, 1996

[51] Int. Cl.[6] ............... C12N 15/53; C12N 9/02; C12N 15/63; C12N 15/70

[52] U.S. Cl. .......... 536/23.2; 536/24.3; 435/69.1; 435/189; 435/252.3; 435/320.1

[58] Field of Search .................. 435/189, 69.1, 435/252.3, 320.1, 6; 536/23.2, 24.3; 514/438; 424/484

[56] References Cited

U.S. PATENT DOCUMENTS 5,051,534  9/1991  Angelastro et al. ............ 568/579
5,444,084  8/1995  Tsuchiya et al. .............. 514/438

FOREIGN PATENT DOCUMENTS 0 318 860   6/1989   European Pat. Off. .
7-194381    8/1995   Japan .
2 271 109   4/1994   United Kingdom .
93/24478   12/1993   WIPO .
96/09287    4/1996   WIPO .

OTHER PUBLICATIONS

Grunler, J., et al., "Branch–point reactions in the biosynthesis of cholesterol, dolichol, ubiquinone and prenylated proteins" *Biochim. Biophys. Acta*, 1212:259–277 (1994).

Glomset, J.A., et al., "Prenyl proteins in eukaryotic cells: a new type of membrane anchor" *Trends Biochem. Sci.*, 15:139–142 (1990).

Kinsella, B.T., et al., "rab GTP–binding Proteins with Three Different Carboxyl–terminal Cysteine Motifs Are Modified in Vivo by 20–Carbon Isoprenoids" *J. Biol. Chem.*, 267:3940–3945 (1992).

Shen, B.Q., et al., "Effects of Lovastatin on Trafficking of Cystic Fibrosis Transmembrane Conductance Regulator in Human Tracheal Epithelium" *J. Biol. Chem.*, 270:25102–25106 (1995).

Pittler, S.J., et al., "In Vivo Requirement of Protein Prenylation for Maintenance of Retinal Cytoarchitecture and Photoreceptor Structure" *J. Cell Biol.*, 130:431–439 (1995).

Kosuga, K., et al., "Nucleotide sequence of a cDNA for mouse squalene epoxidase" *Biochim. Biophys. Acta*, 1260:345–348 (1995).

Sakakibara, J., et al., "Molecular Cloning and Expression of Rat Squalene Epoxidase" *J. Biol. Chem.*, 270:17–20 (1995).

Robinson, G. W., et al., Molecular and Celular Biology, vol. 13, "Conservation between human and fungal squalene synthetases: Similarities in structure, function and regulation", pp. 2706–2717, 1993.

(List continued on next page.)

*Primary Examiner*—Rebecca E. Prouty
*Assistant Examiner*—William W. Moore
*Attorney, Agent, or Firm*—Incyte Pharmaceuticals, Inc.

[57] ABSTRACT

The present invention provides a human squalene epoxidase (HSQEP) and polynucleotides which identify and encode HSQEP. The invention also provides genetically engineered expression vectors and host cells comprising the nucleic acid sequences encoding HSQEP and a method for producing HSQEP. The invention also provides for the use of HSQEP and agonists, antibodies, or antagonists specifically binding HSQEP, in the prevention and treatment of diseases associated with expression of HSQEP. Additionally, the invention provides for the use of antisense molecules to polynucleotides encoding HSQEP for the treatment of diseases associated with the expression of HSQEP. The invention also provides diagnostic assays which utilize the polynucleotide, or fragments or the complement thereof, and antibodies specifically binding HSQEP.

3 Claims, 8 Drawing Sheets

OTHER PUBLICATIONS

Morrell, P., et al., NeuroToxicology, vol. 15, "Gene expression during Tellurium–induced prmary demyelination", pp. 171–180, 1994.

LoGrasso, P. V., et al., Bioorganic Chemistry, vol. 22, "Comparison of the inhibition of yeast, rat, and human squalene synthetase", pp. 294–299, 1994.

Nagumo, A., et al., Journal of Lipid Research, vol. 36, "Purification and characterization of recombinant squalene epoxidase", pp. 1489–1497, 1995.

Toews, A. D., et al., Journal of Lipid Research, vol. 37, "Tissue–specific coordinate regulation of enzymes of cholesterol biosynthesis: sciatic nerve versus liver", pp. 2502–2509, 1996.

Nakamura, Y., et al., The Journal of Biological Chemistry, vol. 271, "Transcriptional regulation of squalene epoxidase by sterols and inhibitors in HeLa cells", pp. 8053–8056, 1996.

```
                   9              18              27              36              45              54
5'    T  TCG  CCA  GCT  CCC  CGG  ATT  GAA  GGT  TGC  CTG  GAG  CCG  CAC  TCT  TGA  GTC  CGA 63              72              81              90              99             108
      GGC  CAT  CTT  TTG  TTG  GAG  AAG  GCG  TCG  GCG  TTG  GCG  TTT  TCC  CGA  GGT  TGG  GCT 117             126             135             144             153             162
      GTA  CAG  TGT  CTC  CGT  CCG  CGG  AAA  AAG  AAG  CCT  CTG  AAC  CCG  CGC  CGG  TCC  GCA 171             180             189             198             207             216
      GCC  CCC  GTG  CCT  TCC  GGA  CGC  TGC  TCG  CCG  TCG  CCA  GAG  GCT  AGG  CCA  CGT  TTC 225             234             243             252             261             270
      CCC  CAG  TGT  CGA  GGT  GTT  TCT  GCG  ACC  CTC  CCT  CCA  CTC  CCA  TTC  CCT  TCT  GAA 279             288             297             306             315             324
      AGG  GCA  CCT  GCT  CTT  GGT  GAG  AAA  AGA  AAT  TAT  CGC  ACG  AAG  AGC  CAG  TAT  CAG 333             342             351             360             369             378
      AAG  AGT  ATC  CAT  CAC  CCG  CAG  CAA  CCG  CTC  AGG  GAA  CAC  CAT  CAA  AAA  AGA  AAA 387             396             405             414             423             432
      AAA  GGG  AAT  ATC  TGG  ATT  TCC  TGG  GCG  AGG  AGG  AGC  GAG  TCT  GCT  CGG  GAG  CTG 441             450             459             468             477             486
      TTC  CAG  CAG  GCG  ATT  TTT  AAA  TAC  TGC  TTT  CTA  CGC  CCT  ATA  CAA  CTT  GGC  TTC 495             504             513             522             531             540
      ACA  TAC  TTT  TAC  ACT  AAC  TTT  ATA  TGA  TTT  TTA  AAA  ACT  GGT  CTG  ATC  GGA  CTT 549             558             567             576             585             594
      CTC  GTC  CTG  GGA  CAC  TGT  TTA  CTG  GAG  TCT  GGC  CGG  CTC  TCC  GTG  CTC  CTC  TTG 603             612             621             630             639             648
      GTA  CCT  CAT  TTG  GGG  GAG  AAC  CTT  AAA  CCC  ACT  CGA  GCA  GAT  AAT  CTC  CGC  CTT 657             666             675             684             693             702
      GAC  CGG  TGC  CAC  CAA  AGA  AGC  CTT  GGA  ACC  ATG  TGG  ACT  TTT  CTG  GGC  ATT  GCC
                                                             M    W    T    F    L    G    I    A 711             720             729             738             747             756
      ACT  TTC  ACC  TAT  TTT  TAT  AAG  AAG  TTC  GGG  GAC  TTC  ATC  ACT  TTG  GCC  AAC  AGG
       T    F    T    Y    F    Y    K    K    F    G    D    F    I    T    L    A    N    R 765             774             783             792             801             810
      GAG  GTC  CTG  TTG  TGC  GTG  CTG  GTG  TTC  CTC  TCG  CTG  GGC  CTG  GTG  CTC  TCC  TAC
       E    V    L    L    C    V    L    V    F    L    S    L    G    L    V    L    S    Y
```

FIGURE 1A

```
         819           828           837           846           855           864
CGC TGT CGC CAC CGA AAC GGG GGT CTC CTC GGG CGC CAG AAG AGC GGC TCC CAG
 R   C   R   H   R   N   G   G   L   L   G   R   Q   K   S   G   S   Q 873           882           891           900           909           918
ATC GCC CTC TTC TCG GAT ATT CTC TCA GGC CTG CCT TTC ATT GGC TTC TTC TGG
 I   A   L   F   S   D   I   L   S   G   L   P   F   I   G   F   F   W 927           936           945           954           963           972
GCA AAT CCC CCC CTG AAT CAG AAA ATA AGG AGC AGC TCG AGG CAG GAG GCG CAG
 A   N   P   P   L   N   Q   K   I   R   S   S   S   R   Q   E   A   Q 981           990           999          1008          1017          1026
AAA AGG AAC CAA TAT TTC AGA AAC AAG CTT AAT AGG AAC AGC TGC TGT ACA TCA
 K   R   N   Q   Y   F   R   N   K   L   N   R   N   S   C   C   T   S 1035          1044          1053          1062          1071          1080
ACA TCT TCT CAG AAT GAC CCA GAA GTT ATC ATC GTG GGA GCT GGC GTG CTT GGC
 T   S   S   Q   N   D   P   E   V   I   I   V   G   A   G   V   L   G 1089          1098          1107          1116          1125          1134
TCT GCT TTG GCA GCT GTG CTT TCC AGA GAT GGA AGA AAG GTG ACA GTC ATT GAG
 S   A   L   A   A   V   L   S   R   D   G   R   K   V   T   V   I   E 1143          1152          1161          1170          1179          1188
AGA GAC TTA AAA GAG CCT GAC AGA ATA GTT GGA GAA TTC CTG CAG CCG GGT GGT
 R   D   L   K   E   P   D   R   I   V   G   E   F   L   Q   P   G   G 1197          1206          1215          1224          1233          1242
TAT CAT GTT CTC AAA GAC CTT GGT CTT GGA GAT ACA GTG GAA GGT CTT GAT GCC
 Y   H   V   L   K   D   L   G   L   G   D   T   V   E   G   L   D   A 1251          1260          1269          1278          1287          1296
CAG GTT GTA AAT GGT TAC ATG ATT CAT GAT CAG GAA AGC AAA TCA GAG GTT CAG
 Q   V   V   N   G   Y   M   I   H   D   Q   E   S   K   S   E   V   Q 1305          1314          1323          1332          1341          1350
ATT CCT AAC CCT CTG TCA GAA AAC AAT CAA GTG CAG AGT GGA AGA GCT TTC CAC
 I   P   N   P   L   S   E   N   N   Q   V   Q   S   G   R   A   F   H 1359          1368          1377          1386          1395          1404
CAC GGA AGA TTC ATC ATG AGT CTC CGG AAA GCA GTT ATG GCA GAG CCC AAT GCA
 H   G   R   F   I   M   S   L   R   K   A   V   M   A   E   P   N   A 1413          1422          1431          1440          1449          1458
AAG TTT ATT GAA GGT GTT GTG TTA CAG TTA TTA GAG GAA GAT GAT GTT GTG ATG
 K   F   I   E   G   V   V   L   Q   L   L   E   E   D   D   V   V   M 1467          1476          1485          1494          1503          1512
GGA GTT CAG CAC AAG GAT AAA GAG ACT GGA GAT ATC AAG GAA CTC CAT GCT CCA
 G   V   Q   H   K   D   K   E   T   G   D   I   K   E   L   H   A   P 1521          1530          1539          1548          1557          1566
CTG ACT GTT GTT GCA GAT GGG CTT TTC TCC AAG TTC AGG AAA AGC CTG GTC TCC
 L   T   V   V   A   D   G   L   F   S   K   F   R   K   S   L   V   S 1575          1584          1593          1602          1611          1620
AAT AAA GTT TCT GTA TCA TCT CAT TTT GTT GGC TTT CTT ATG AAG AAT GCA CCA
 N   K   V   S   V   S   S   H   F   V   G   F   L   M   K   N   A   P
```

FIGURE 1B

```
      1629            1638            1647            1656            1665            1674
CAG TTT ACA GCA AAT CAT GCT GAA CTT ATT TTA GCT AAC CCG AGT CCA GTT CTC
 Q   F   T   A   N   H   A   E   L   I   L   A   N   P   S   P   V   L 1683            1692            1701            1710            1719            1728
ATC TAC CAG ATT TCA TCC AGT GAA ATC GAG TAC TTG TTG ACA TTA GAG GGA ATG
 I   Y   Q   I   S   S   S   E   I   E   Y   L   L   T   L   E   G   M 1737            1746            1755            1764            1773            1782
CCA AGG AAT TTA AGA GAA TAC ATG GTT GAA AAA ATT TAC CCA CAA ATA CCT GAT
 P   R   N   L   R   E   Y   M   V   E   K   I   Y   P   Q   I   P   D 1791            1800            1809            1818            1827            1836
CAC CTG AAA GAA CCA TTC TTA GAA GCC ACT GAC AAT TCT CAT CTG AGG TCC ATG
 H   L   K   E   P   F   L   E   A   T   D   N   S   H   L   R   S   M 1845            1854            1863            1872            1881            1890
CCA GCA AGC TTC CTT CCT CCT TCA TCA GTG AAG AAA CGA GGT GTT CTT CTT TTG
 P   A   S   F   L   P   P   S   S   V   K   K   R   G   V   L   L   L 1899            1908            1917            1926            1935            1944
GGA GAC GCA TAT AAT ATG AGG CAT CCA CTT ACT GGT GGA GGA ATG ACT GTT GCT
 G   D   A   Y   N   M   R   H   P   L   T   G   G   G   M   T   V   A 1953            1962            1971            1980            1989            1998
TTT AAA GAT ATA AAA CTA TGG AGA AAA CTG CTA AAG GGT ATC CCT GAC CTT TAT
 F   K   D   I   K   L   W   R   K   L   L   K   G   I   P   D   L   Y 2007            2016            2025            2034            2043            2052
GAT GAT GCA GCT ATT TTC GAG GCC AAA AAA TCA TTT TAC TGG GCA AGA AAA ACA
 D   D   A   A   I   F   E   A   K   K   S   F   Y   W   A   R   K   T 2061            2070            2079            2088            2097            2106
TCT CAT TCC TTT GTC GTG AAT ATC CTT GCT CAG GCT CTT TAT GAA TTA TTT TCT
 S   H   S   F   V   V   N   I   L   A   Q   A   L   Y   E   L   F   S 2115            2124            2133            2142            2151            2160
GCC ACA GAT GAT TCC CTG CAT CAA CTA AGA AAA GCC TGT TTT CTT TAT TTC AAA
 A   T   D   D   S   L   H   Q   L   R   K   A   C   F   L   Y   F   K 2169            2178            2187            2196            2205            2214
CTT GGT GGC GAA TGT NTT GCG GGT CCT GTT GGG CTG CTT TCT GTA TTG TCT CCT
 L   G   G   E   C   X   A   G   P   V   G   L   L   S   V   L   S   P 2223            2232            2241            2250            2259            2268
AAC CCT CTA GTT TTA ATT GGA CAC TTC TTT GCT GTT GCA ATC TAT GCC GTG TAT
 N   P   L   V   L   I   G   H   F   F   A   V   A   I   Y   A   V   Y 2277            2286            2295            2304            2313            2322
TTT TGC TTT AAG TCA GAA CCT TGG ATT ACA AAA CCT CGA GCC CTT CTC AGT AGT
 F   C   F   K   S   E   P   W   I   T   K   P   R   A   L   L   S   S 2331            2340            2349            2358            2367            2376
GGT GCT GTA TTG TAC AAA GCG TGT TCT GTA ATA TTT CCT CTA ATT TAC TCA GAA
 G   A   V   L   Y   K   A   C   S   V   I   F   P   L   I   Y   S   E 2385            2394            2403            2412            2421            2430
ATG AAG TAT ATG GTT CAT TAA GCT TAA AGG GGA ACC ATT TGT GAA TGA ATA TTT
 M   K   Y   M   V   H

2439
GGA ACT TAC CAA GTC  3'
```

```
359 V E K I Y P Q I P D H L K E P F L E A T D N S H L R S M P A S F L P P S S V K K    HSQEP
359 A E Q I Y P Q L P E H L K E S F L E A S Q N G R L R T M P A S F L P P S S V N K    GI 1217593
360 T E Q I Y P Q I P D H L K E S F L E A C Q N A R L R T M P A S F L P P S S V N K    GI 1083804

399 R G V L L L G D A Y N M R H P L T G G G M T V A F K D I K L W R K L L K G I P D    HSQEP
399 R G V L I L G D A Y N L R H P L T G G G M T V A L K D I K L W R Q L L K D I P D    GI 1217593
400 R G V L L L G D A Y N L R H P L T G G G M T V A L K D I K I W R Q L L K D I P D    GI 1083804

439 L Y D D A A I F E A K K S F Y W A R K T S H S F V V N I L A Q A L Y E L F S A T    HSQEP
439 L Y D D A A I F Q A K K S F F W S R K R T H S F V V N V L A Q A L Y E L F S A T    GI 1217593
440 L Y D D A A I F Q A K K S F F W S R K R S H S F V V N V L A Q A L Y E L F S A T    GI 1083804

479 D D S L H Q L R K A C F L Y F K L G G E C I A G P V G L L S V L S P N P L V L I    HSQEP
479 D D S L H Q L R K A C F L Y F K L G G E C V T G P V G L L S I I L S P H P L V L I    GI 1217593
480 D D S L R Q L R K A C F L Y F K L G G E C L T G P V G L L S I I L S P D P L L L I    GI 1083804

519 G H F F A V A I Y A V Y F C F K S E P W I T K P R A L L S S G A V L Y K A C S V    HSQEP
519 R H F F S V A I Y A T Y F C F K S E P W A T K P R A L F S S G A V L Y K A C S I    GI 1217593
520 R H F F S V A V Y A T Y F C F K S E P W A T K P R A L F S S G A I L Y K A C S I    GI 1083804

559 L F P L I Y S E M K Y M V H                                                         HSQEP
559 L F P L I Y S E M K Y L V H                                                         GI 1217593
560 L F P L I Y S E M K Y L V H                                                         GI 1083804
```

FIGURE 2B

HUMAN SQUALENE EPOXIDASE

FIELD OF THE INVENTION

This invention relates to nucleic acid and amino acid sequences of a novel squalene epoxidase and to the use of these sequences in the diagnosis, prevention, and treatment of diseases such as hypercholesterolemia and atherosclerosis.

BACKGROUND OF THE INVENTION

The de novo biosynthesis of cholesterol in the endoplasmic reticulum proceeds by a multistep process. Acetyl coenzyme A (-CoA) is condensed and converted to 3-hydroxy 3-methylgutaryl (HMG)-CoA. HMG-CoA is reduced to mevalonate by the action of HMG-CoA reductase. In consecutive enzyme-catalyzed reactions, mevalonate is converted to isopentenyl pyrophosphate (IPPP), geranyl pyrophosphate (GPP), farnesyl pyrophosphate (FPP) and squalene. Squalene is oxidized to squalene 2,3-epoxide by squalene epoxidase. Rearrangements of squalene 2,3-epoxide lead to lanosterol. Lanosterol is converted to cholesterol in the endoplasmic reticulum in another series of enzymatic reactions.

HMG-CoA reductase is considered one of the major regulatory enzymes in cholesterol biosynthesis. HMG-CoA reductase inhibitors such as lovastatin are widely used to lower plasma cholesterol levels. Since the HMG-CoA reductase-catalyzed production of mevalonate is an early step in the cholesterol biosynthetic pathway, HMG-CoA reductase inhibition depletes many other intermediates of the cholesterol biosynthetic pathway.

Many intermediates in the cholesterol biosynthetic pathway depleted by inhibition of HMG-CoA reductase have additional roles in cellular function. For instance, FPP and FPP-derived geranylgeranyl pyrophosphate (GGPP) covalently modify proteins, heme, and tRNA, and are precursors for biologically important molecules such as dolichols and ubiquinones (Grunler, J. et al. (1994) Biochim. Biophys. Acta 1212:259–277). Posttranslational protein isoprenylation promotes the anchoring of proteins to membranes and serves as a regulatory signal (Glomset, J. A. et al. (1990) Trends Biochem. Sci. 15:139–142). For example, the Rab proteins are a class of small GTP binding proteins which are involved in intracellular vesicle trafficking. Isoprenylated Rab proteins on the surface of vesicles interact with GTPase-activating proteins and specific Rab receptors on the target membrane, leading to membrane fusion. When cellular isoprenoid synthesis is blocked by lovastatin, Rab proteins that are normally localized in membranes of the endoplasmic reticulum, Golgi apparatus, and endosomes accumulate in the cytosol (Kinsella B. T. et al. (1992) J. Biol. Chem. 267:3940–3945).

Defects in protein isoprenylation caused by depletion of FPP and its metabolites may have undesirable biological consequences. The vesicular trafficking of integral membrane proteins is compromised by altered Rab isoprenylation resulting from depletion of intracellular FPP and GGPP. For instance, cystic fibrosis transmembrane conductance regulator (CFTR) function in a primary human airway epithelial cell line is compromised by lovastatin (Shen, B.-Q. et al. (1995) J Biol. Chem. 270:25102–25106). Lovastatin is proposed to disrupt the trafficking of CFTR to the apical plasma membrane by inhibiting the isoprenylation of Rab or Rab-like trafficking proteins. Protein isoprenylation is also important in the maintenance of retinal cytoarchitecture. Lovastatin produces profound dysplasic-like changes in adult rat retinas primarily in the photoreceptor layer (Pittler, S. J. et al. (1995) J. Cell Biol. 130:431–439). This retinal degeneration is traced to defects in protein isoprenylation.

Arteriosclerosis, a generic term for thickening and hardening of the arterial wall, is responsible for the majority of deaths in the United States and most westernized societies. One type of arteriosclerosis is atherosclerosis, the disorder of the larger arteries that underlies most coronary artery disease, aortic aneurysm, and arterial disease of the lower extremities and also plays a major role in cerebrovascular disease. Atherosclerosis is by far the leading cause of death in the U.S., both above and below age 65 and in both sexes.

A generally accepted theory for the pathogenesis of atherosclerosis is the reaction to injury hypothesis. According to this idea, the endothelial cells lining the intima are exposed to repeated or continuing insults to their integrity. Injury to the endothelium includes metabolic injury, such as chronic hypercholesterolemia. Reduction of hypercholesterolemia results in a decrease in the progression of atherosclerosis in humans and other primates. Drugs that act primarily by lowering low density lipoprotein (LDL) cholesterol are the current drugs of choice for high-risk patients.

It is apparent that, while inhibitors of enzymes at early steps in the cholesterol biosynthetic pathway are effective cholesterol-lowering therapeutics, such inhibitors also deplete other necessary metabolic intermediates. Inhibitors of enzymes which are further along the cholesterol biosynthetic pathway would therefore provide more desirable cholesterol-lowering therapeutics than the inhibitors of earlier pathway enzymes such as HMG-CoA reductase.

The discovery of polynucleotides encoding human squalene epoxidase, and the molecules themselves, presents opportunities to investigate the regulation and control of the later (post-FPP) cholesterol biosynthetic pathway and to elucidate mechanisms for the reduction of hypercholesterolemia in humans. Discovery of molecules related to squalene epoxidase satisfies a need in the art by providing new diagnostic or therapeutic compositions useful in the reduction of LDL cholesterol, a key risk factor in atherosclerosis and coronary heart disease.

SUMMARY OF THE INVENTION

The present invention features a human squalene epoxidase hereinafter designated HSQEP and characterized as having chemical and structural homology to squalene epoxidase from rat and mouse. Accordingly, the invention features a substantially purified HSQEP having the amino acid sequence, SEQ ID NO:1.

One aspect of the invention features isolated and substantially purified polynucleotides that encode HSQEP. In a particular aspect, the polynucleotide is the nucleotide sequence of SEQ ID NO:2.

The invention also relates to a polynucleotide sequence comprising the complement of SEQ ID NO:2 or variants thereof. In addition, the invention features polynucleotide sequences which hybridize under stringent conditions to SEQ ID NO:2.

The invention additionally features nucleic acid sequences encoding polypeptides, oligonucleotides, peptide nucleic acids (PNA), fragments, portions or antisense molecules thereof, and expression vectors and host cells comprising polynucleotides that encode HSQEP. The present invention also features antibodies which bind specifically to HSQEP, and pharmaceutical compositions comprising substantially purified HSQEP. The invention also features the use of agonists and antagonists of HSQEP.

BRIEF DESCRIPTION OF THE FIGURES

FIGS. 1A, 1B, and 1C show the amino acid sequence (SEQ ID NO:1) and nucleic acid sequence (SEQ ID NO:2) of HSQEP. The alignment was produced using MACDNASIS PRO software (Hitachi Software Engineering Co., Ltd., San Bruno, Calif.).

FIGS. 2A and 2B show the amino acid sequence alignments among HSQEP (SEQ ID NO:1), squalene epoxidase from mouse (GI 1217593; SEQ ID NO:3), and from rat (GI 1083804; SEQ ID NO:4). The alignment was produced using the multisequence alignment program of DNASTAR™ software (DNASTAR Inc, Madison Wis.).

DESCRIPTION OF THE INVENTION

Figure 3:
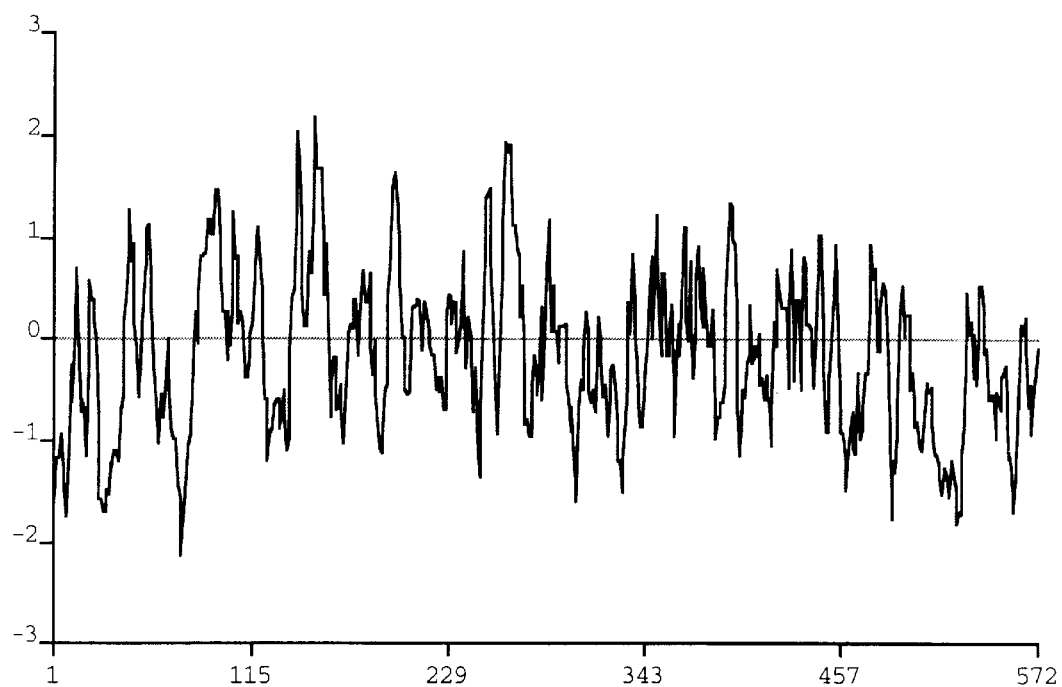
FIG. 3 shows the hydrophobicity plot (MACDNASIS PRO software) for HSQEP, SEQ ID NO: 1; the positive X axis reflects amino acid position, and the negative Y axis, hydrophobicity.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

"Nucleic acid sequence" as used herein refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence and fragments or portions thereof, of a naturally occurring or synthetic molecule.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

HSQEP, as used herein, refers to the amino acid sequences of substantially purified HSQEP obtained from any species, particularly mammalian, including bovine, ovine, porcine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR™ (Perkin Elmer, Norwalk, Conn.) in the 5' and/or the 3' direction and resequenced, or which has been assembled from the overlapping sequences of more than one Incyte clone using the GELVIEW FRAGMENT ASSEMBLY system (GCG, Madison, Wis.), or which has been both extended and assembled.

A "variant" of HSQEP, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic HSQEP, or any oligopeptide thereof, to induce a specific immune response in appropriate animals or cells and to bind with specific antibodies.

The term "agonist", as used herein, refers to a molecule which, when bound to HSQEP, causes a change in HSQEP which modulates the activity of HSQEP. Agonists may include proteins, nucleic acids, carbohydrates, or any other molecules which bind to HSQEP.

The terms "antagonist" or "inhibitor", as used herein, refer to a molecule which, when bound to HSQEP, blocks the biological or immunological activity of HSQEP. Antagonists and inhibitors may include proteins, nucleic acids, carbohydrates, or any other molecules which bind to HSQEP.

The term "modulate", as used herein, refers to a change or an alteration in the biological activity of HSQEP. Modulation may be an increase or a decrease in protein activity, a change in binding characteristics, or any other change in the biological, functional or immunological properties of HSQEP.

The term "mimetic", as used herein, refers to a molecule, the structure of which is developed from knowledge of the structure of HSQEP or portions thereof and, as such, is able to effect some or all of the actions of squalene epoxidase-like molecules.

The term "derivative", as used herein, refers to the chemical modification of a nucleic acid encoding HSQEP or the encoded HSQEP. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual,* Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen binds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides by base-pairing. For example, for the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO: 1" encompasses the full-length human HSQEP and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding HSQEP or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 by northern analysis is indicative of the presence of mRNA encoding HSQEP in a sample and thereby correlates with expression of the transcript from the polynucleotide encoding the protein.

"Alterations" in the polynucleotide of SEQ ID NO: 2, as used herein, comprise any alteration in the sequence of polynucleotides encoding HSQEP including deletions, insertions, and point mutations that may be detected using hybridization assays. Included within this definition is the detection of alterations to the genomic DNA sequence which encodes HSQEP (e.g., by alterations in the pattern of restriction fragment length polymorphisms capable of hybridizing to SEQ ID NO:2), the inability of a selected fragment of SEQ ID NO: 2 to hybridize to a sample of genomic DNA (e.g., using allele-specific oligonucleotide probes), and improper or unexpected hybridization, such as hybridization to a locus other than the normal chromosomal locus for the polynucleotide sequence encoding HSQEP (e.g., using fluorescence in situ hybridization (FISH) to metaphase chromosomes spreads).

As used herein, the term "antibody" refers to intact molecules as well as fragments thereof, such as Fab, F(ab')$_2$, and Fv, which are capable of binding the epitopic determinant. Antibodies that bind HSQEP polypeptides can be prepared using intact polypeptides or fragments containing small peptides of interest as the immunizing antigen. The polypeptide or peptide used to immunize an animal can be derived from translated RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

THE INVENTION

The invention is based on the discovery of a novel human squalene epoxidase (HSQEP), the polynucleotides encoding HSQEP, and the use of these compositions for the diagnosis, prevention, or treatment of hypercholesterolemia and atherosclerosis.

Nucleic acids encoding the human HSQEP of the present invention were first identified in Incyte Clone 638884 from a cDNA library prepared from noncancerous breast tissue removed from a 54-year-old female during a bilateral radical mastectomy (BRSTNOT03) through a computer-generated search for amino acid sequence alignments. A consensus sequence, SEQ ID NO:2, was derived from the following overlapping and/or extended nucleic acid sequences: Incyte Clones 1338208 (COLNNOT13); 000594 (U937NOT01); 013083 (THP1PLB01); 1438629 (PANCNOT08); 043115 (TBLYNOT01); 1434076 (BEPINON01); 1440965 (THYRNOT03); 638884 (BRSTNOT03); and 790619 (PROSTUT03).

Figure 2A:
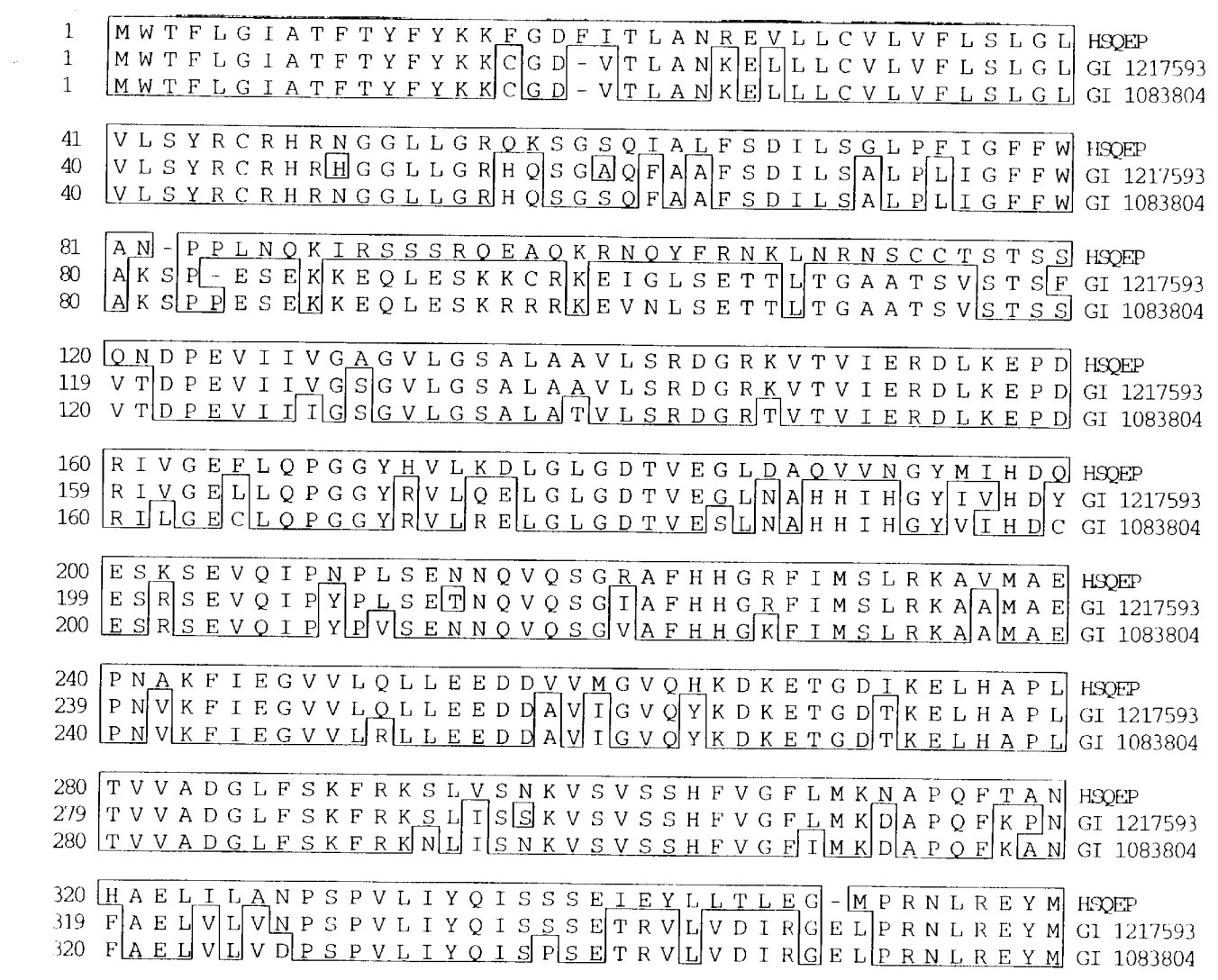
Figure 4:
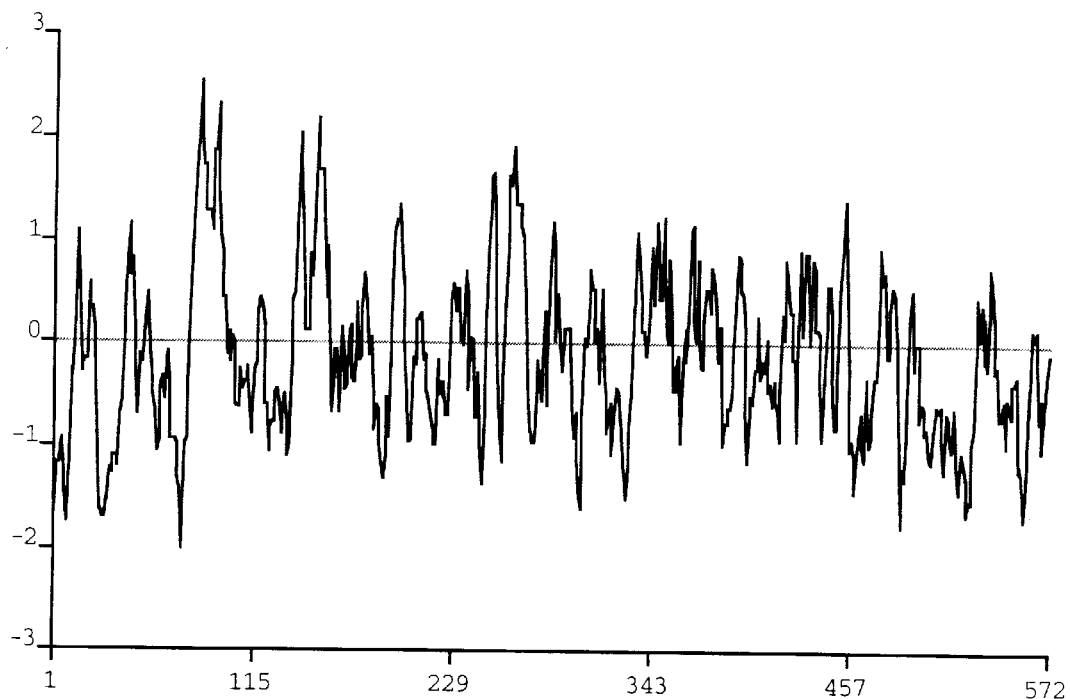
FIG. 4 shows the hydrophobicity plot for mouse squalene epoxidase, SEQ ID NO:3.

In one embodiment, the invention encompasses the novel human squalene epoxidase, a polypeptide comprising the amino acid sequence of SEQ ID NO:1, as shown in FIGS. 1A, 1B, and 1C. HSQEP is 572 amino acids in length. HSQEP has chemical and structural homology with mouse squalene epoxidase (GI 1217593; SEQ ID NO:3) and rat squalene epoxidase (GI 1083804; SEQ ID NO:4). In particular, HSQEP and mouse squalene epoxidase share 79% identity, while HSQEP and rat squalene epoxidase share 78% identity (FIGS. 2A and 2B). As illustrated by FIGS. 3 and 4, HSQEP and mouse squalene epoxidase have similar hydrophobicity plots. From its amino acid sequence homology with the mouse and rat homologs, HSQEP is predicted to contain a transmembrane domain extending from $I_{21}$ to $V_{41}$ of SEQ ID NO: 1. In addition, HSQEP contains a putative FAD binding domain extending from $I_{126}$ to $E_{152}$ of SEQ ID NO:1. HSQEP catalyzes the oxidation of squalene to squalene 2,3-epoxide (FIG. 5) in the presence of oxygen, FAD, and NADPH.

Many enzymes of the cholesterol biosynthetic pathway are regulated at the transcriptional level. In particular, transcription of these enzymes tends to be up-regulated in the absence of cholesterol in the bloodstream, due to a low-fat diet or treatment with cholesterol-lowering therapeutics. Northern analysis shows that HSQEP transcription appears to follow that trend. Sequences encoding full-length HSQEP were found in thyroid tumor tissue (THYRNOT03) obtained from a donor with a past history of hypercholesterolemia. The donor may have decreased his dietary fat intake and/or have been taking cholesterol-lowering drugs. Sequences encoding full-length HSQEP were also found in healthy colon tissue from a donor with ulcerative colitis. The donor was being treated with anabolic steroids, which may up-regulate transcription of HSQEP. Sequences encoding full-length HSQEP were also found in inflamed adenoid tissue from a three-year old child, a bronchial epithelium primary cell line, and hybrid T-B lymphocytes from a leukemic cell line. It must be noted that expression of HSQEP is not necessarily limited to these tissues.

The invention also encompasses HSQEP variants. A preferred HSQEP variant is one having at least 80%, and more preferably 90%, amino acid sequence similarity to the HSQEP amino acid sequence (SEQ ID NO:1). A most preferred HSQEP variant is one having at least 95% amino acid sequence similarity to SEQ ID NO:1.

The invention also encompasses polynucleotides which encode HSQEP. Accordingly, any nucleic acid sequence which encodes the amino acid sequence of HSQEP can be used to generate recombinant molecules which express HSQEP. In a particular embodiment, the invention encompasses the polynucleotide comprising the nucleic acid of SEQ ID NO:2 as shown in FIGS. 1A, 1B, and 1C.

It will be appreciated by those skilled in the art that as a result of the degeneracy of the genetic code, a multitude of nucleotide sequences encoding HSQEP, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring HSQEP, and all such variations are to be considered as being specifically disclosed.

Although nucleotide sequences which encode HSQEP and its variants are preferably capable of hybridizing to the nucleotide sequence of the naturally occurring HSQEP under appropriately selected conditions of stringency, it may be advantageous to produce nucleotide sequences encoding HSQEP or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding HSQEP and its derivatives without altering the encoded amino acid sequences include the production of RNA transcripts having more desirable properties, such as a greater half-life, than transcripts produced from the naturally occurring sequence.

The invention also encompasses production of a DNA sequence, or portions thereof, which encode HSQEP and its derivatives, entirely by synthetic chemistry. After production, the synthetic gene may be inserted into any of the many available DNA vectors and cell systems using reagents that are well known in the art at the time of the filing of this application. Moreover, synthetic chemistry may be used to introduce mutations into a sequence encoding HSQEP or any portion thereof.

Also encompassed by the invention are polynucleotide sequences that are capable of hybridizing to the claimed nucleotide sequences, and in particular, those shown in SEQ ID NO:2, under various conditions of stringency. Hybridization conditions are based on the melting temperature (Tm) of the nucleic acid binding complex or probe, as taught in Kimmel, A. R. (1987; Methods Enzymol. Vol. 152), and may be used at a defined stringency.

Altered nucleic acid sequences encoding HSQEP which are encompassed by the invention include deletions, insertions, or substitutions of different nucleotides resulting in a polynucleotide that encodes the same or a functionally equivalent HSQEP. The encoded protein may also contain deletions, insertions, or substitutions of amino acid residues which produce a silent change and result in a functionally equivalent HSQEP. Deliberate amino acid substitutions may be made on the basis of similarity in polarity, charge, solubility, hydrophobicity, hydrophilicity, and/or the amphipathic nature of the residues as long as the biological activity of HSQEP is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the gene encoding HSQEP. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, SEQUENASE DNA Polymerase (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE AMPLIFICATION SYSTEM GIBCO BRL, Gaithersburg, Md.). Preferably, the process is automated with machines such as the Hamilton Micro Lab 2200 (Hamilton, Reno, Nev.), Peltier THERMAL CYCLER (PTC200; MJ Research, Watertown, Mass.) and the ABI 377 DNA sequencers (Perkin Elmer).

The polynucleotide sequence encoding HSQEP may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO 406 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk in genomic DNA (Clontech, Palo Alto, Calif.). This process avoids the need to screen libraries and may be is useful in finding intron/exon junctions.

When screening for full-length cDNAs, it is preferable to use libraries that have been size-selected to include larger cDNAs. Also, random-primed libraries are preferable in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HSQEP, or fusion proteins or functional equivalents thereof, may be used in recombinant DNA molecules to direct expression of HSQEP in appropriate host cells. Due to the inherent degeneracy of the genetic code, other DNA sequences which encode substantially the same or a functionally equivalent amino acid sequence may be produced and these sequences may be used to clone and express HSQEP.

As will be understood by those of skill in the art, it may be advantageous to produce HSQEP-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter the HSQEP coding sequence for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequence. For example, site-directed mutagenesis may be used to insert new restriction sites, alter glycosylation patterns, to change codon preference, to produce splice variants, or other mutations, and so forth.

In another embodiment of the invention, a natural, modified, or recombinant polynucleotide encoding HSQEP may be ligated to a heterologous sequence to encode a fusion protein. For example, to screen peptide libraries for inhibitors of HSQEP activity, it may be useful to encode a chimeric HSQEP protein that can be recognized by a commercially available antibody. A fusion protein may also be engineered to contain a cleavage site located between a HSQEP encoding sequence and the heterologous protein sequence, so that HSQEP may be cleaved and purified away from the heterologous moiety.

In another embodiment, the coding sequence of HSQEP may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the HSQEP amino acid sequence, or a portion thereof. For example, peptide synthesis can be performed using various solid-phase techniques (Roberge, J. Y. et al. (1995) Science 269:202–204) and automated synthesis may be achieved, for example, using the ABI 431A PEPTIDE SYNTHESIZER (Perkin Elmer).

The newly synthesized peptide may be substantially purified by preparative high performance liquid chromatography (e.g., Creighton, T. (1983) *Proteins, Structures and Molecular Principles,* WH Freeman and Co., New York, N.Y.). The composition of the synthetic peptides may be confirmed by amino acid analysis or sequencing (e.g., the Edman degradation procedure; Creighton, supra). Additionally, the amino acid sequence of HSQEP, or any part thereof, may be altered during direct synthesis and/or combined using chemical methods with sequences from other proteins, or any part thereof, to produce a variant polypeptide.

In order to express a biologically active HSQEP, the nucleotide sequence encoding HSQEP or functional equivalents, may be inserted into an appropriate expression vector, i.e., a vector which contains the necessary elements for the transcription and translation of the inserted coding sequence.

Methods which are well known to those skilled in the art may be used to construct expression vectors containing a HSQEP coding sequence and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual,* Cold Spring Harbor Press, Plainview, N.Y., and Ausubel, F. M. et al. (1989) *Current Protocols in Molecular Biology,* John Wiley & Sons, New York, N.Y.

A variety of expression vector/host systems may be utilized to contain and express a HSQEP coding sequence. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT® phagemid (Stratagene, LaJolla, Calif.) or PSPORT plasmid (Gibco BRL) and ptrp-lac hybrids, and the like may be used. The baculovirus polyhedrin promoter may be used in insect cells. Promoters or enhancers derived from the genomes of plant cells. (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HSQEP, vectors based on SV40 or EBV may be used with an appropriate selectable marker.

In bacterial systems, a number of expression vectors may be selected depending upon the use intended for HSQEP. For example, when large quantities of HSQEP are needed for the induction of antibodies, vectors which direct high level expression of fusion proteins that are readily purified may be used. Such vectors include, but are not limited to, the multifinctional *E. coli* cloning and expression vectors such as the BLUESRIPT phagemid (Stratagene), in which the sequence encoding HSQEP may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. PGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of a sequence encoding HSQEP may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express HSQEP. For example, in one such system, *Autographa californica* nuclear polyhedrosis virus (AcNPV) is used as a vector to express foreign genes in *Spodoptera frugiperda* cells or in *Trichoplusia larvae*. The sequence encoding HSQEP may be cloned into a non-essential region of the virus, such as the polyhedrin gene, and placed under control of the polyhedrin promoter. Successful insertion of HSQEP will render the polyhedrin gene inactive and produce recombinant virus lacking coat protein. The recombinant viruses may then be used to infect, for example, *S. frugiperda* cells or *Trichoplusia* larvae in which HSQEP may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, a sequence encoding HSQEP may be ligated into an adenovirus transcription/translation complex consisting of the late promoter and tripartite leader sequence. Insertion in a non-essential E1 or E3 region of the viral genome may be used to obtain a viable virus which is capable of expressing HSQEP in infected host cells (Logan, J. and Shenk, T. (1984) Proc. Natl. Acad. Sci. 81:3655–3659). In addition, transcription enhancers, such as the *Rous sarcoma* virus (RSV) enhancer, may be used to increase expression in mammalian host cells.

Specific initiation signals may also be used to achieve more efficient translation of a sequence encoding HSQEP. Such signals include the ATG initiation codon and adjacent sequences. In cases where sequences encoding HSQEP, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express HSQEP may be transformed using expression vectors which may contain viral origins of replication and/or endogenous expression elements and a selectable marker gene on the same or separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk⁻ or aprt⁻ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding HSQEP is inserted within a marker gene sequence, recombinant cells containing sequences encoding HSQEP can be identified by the absence of marker gene function. Alternatively, a marker gene can be placed in tandem with a sequence encoding HSQEP under the control of a single promoter. Expression of the marker gene in response to induction or selection usually indicates expression of the tandem gene as well.

Alternatively, host cells which contain the coding sequence for HSQEP and express HSQEP may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of the nucleic acid or protein.

The presence of the polynucleotide sequence encoding HSQEP can be detected by DNA-DNA or DNA-RNA hybridization or amplification using probes or portions or fragments of polynucleotides encoding HSQEP. Nucleic acid amplification based assays involve the use of oligonucleotides or oligomers based on the HSQEP-encoding sequence to detect transformants containing DNA or RNA encoding HSQEP. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of HSQEP, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on HSQEP is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HSQEP include oligolabeling, nick translation, end-labeling or PCR amplification using a labeled nucleotide. Alternatively, the sequence encoding HSQEP, or any portion of it, may be cloned into a vector for the production of an MRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison, Wis.); and U.S. Biochemical Corp., (Cleveland, Ohio)). Suitable reporter molecules or labels, which may be used, include adionuclides, enzymes, fluorescent, chemiluminescent, or chromogenic agents as well as substrates, cofactors, inhibitors, magnetic particles, and the like.

Host cells transformed with a nucleotide sequence encoding HSQEP may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode HSQEP may be designed to contain signal sequences which direct secretion of HSQEP through a prokaryotic or eukaryotic cell membrane. Other recombinant constructions may be used to join sequences encoding HSQEP to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and HSQEP may be used to facilitate purification. One such expression vector provides for expression of a fusion protein containing HSQEP and a nucleic acid encoding 6 histidine residues preceding a thioredoxin or an enterokinase cleavage site. The histidine residues facilitate purification on IMIAC (immobilized metal ion affinity chromatography as described in Porath, J. et al. (1992, Prot. Exp. Purif. 3: 263–281) while the enterokinase cleavage site provides a means for purifying HSQEP from the fusion protein. A discussion of vectors which contain fusion proteins is provided in Kroll, D. J. et al. (1993; DNA Cell Biol. 12:441–453).

In addition to recombinant production, fragments of HSQEP may be produced by direct peptide synthesis using solid-phase techniques (cf Stewart et al. (1969) Solid-Phase Peptide Synthesis, W.H. Freeman Co., San Francisco, Calif.; Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of HSQEP may be chemically synthesized separately and combined using chemical methods to produce the full length molecule

THERAPEUTICS

In another embodiment of the invention, HSQEP or fragments thereof may be used for therapeutic purposes.

Figure 5:
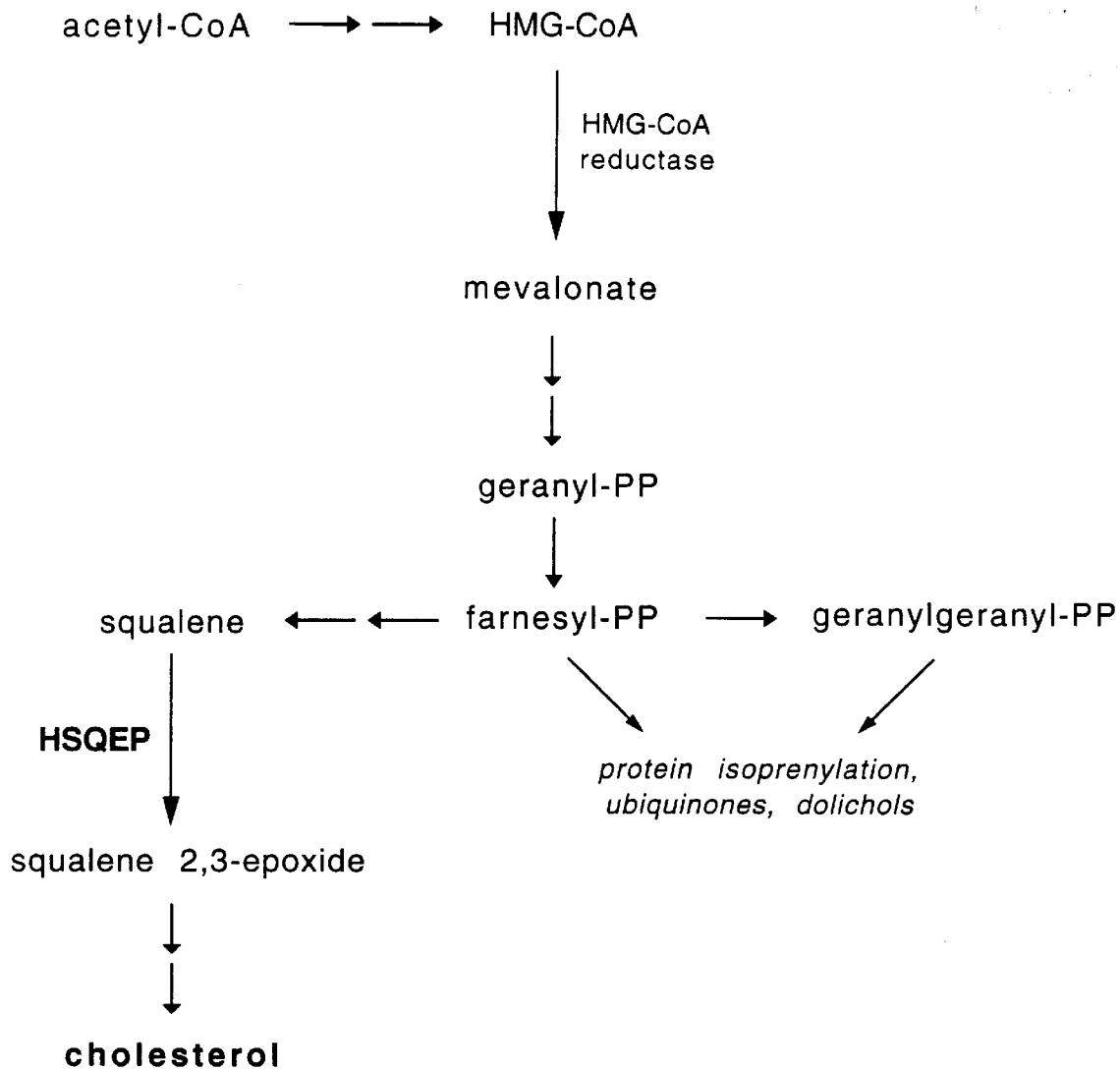
FIG. 5 shows the cholesterol biosynthetic pathway.

As shown in FIG. 5, mevalonate, GPP and FPP are not only precursors of cholesterol, but are also the precursors of mevalonate-derived non-sterol metabolites such as ubiquinones, dolichols, and isoprenoic acids. Lovastatin is a widely-used cholesterol-lowering drug which inhibits HMG-CoA reductase, an enzyme at the early stage in the cholesterol biosynthetic pathway. Consequently, in addition to cholesterol, lovastatin and other HMG-CoA reductase inhibitors deplete the important mevalonate-derived non-sterol metabolites. There is a significant need for anti-hypercholesterolemic therapeutics which do not also deplete the production of mevalonate-derived non-sterol metabolites. Since squalene is much further along the pathway of cholesterol biosynthesis, post-FPP and the non-sterol metabolite branch point (FIG. 5), HSQEP is a much better target for the design of cholesterol-lowering therapeutics than HMG-CoA reductase.

Therefore, in one embodiment, antagonists or inhibitors which block or modulate the activity of HSQEP may be used in those situations where such inhibition is therapeutically desirable. Such antagonists or inhibitors may be produced using a variety of methods which are generally known in the art. In particular, purified HSQEP may be used to screen libraries of pharmaceutical agents for those which specifically bind HSQEP or to produce antibodies.

In one aspect, antibodies which are specific for HSQEP may be used directly as an antagonist, or indirectly as a targeting or delivery mechanism for bringing a pharmaceutical agent to cells or tissue which express HSQEP. The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with HSQEP or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to HSQEP have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of HSQEP amino acids may be fused with those of another protein such as keyhole limpet hemocyanin and antibody produced against the chimeric molecule.

Monoclonal antibodies to HSQEP may be prepared using any technique which provides for the production of antibody molecules by continuous cell lines in culture. These include, but are not limited to, the hybridoma technique, the human B-cell hybridoma technique, and the EBV-hybridoma technique (Koehler et al. (1975) Nature 256:495–497; Kosbor et al. (1983) Immunol. Today 4:72; Cote et al. (1983) Proc. Natl. Acad. Sci. 80:2026–2030; Cole et al. (1985) *Monoclonal Antibodies and Cancer Therapy*, Alan R. Liss Inc., New York, N.Y., pp. 77–96).

In addition, techniques developed for the production of "chimeric antibodies", the splicing of mouse antibody genes to human antibody genes to obtain a molecule with appropriate antigen specificity and biological activity can be used (Morrison et al. (1984) Proc. Natl. Acad. Sci. 81:6851–6855; Neuberger et al. (1984) Nature 312:604–608; Takeda et al. (1985) Nature 314:452–454). Alternatively, techniques described for the production of single chain antibodies may be adapted, using methods known in the art, to produce HSQEP-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, et al. (1989) Proc. Natl. Acad. Sci. 86: 3833–3837; Winter, G. et al. (1991) Nature 349:293–299).

Antibody fragments which contain specific binding sites for HSQEP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse et al. (1989) Science 256:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HSQEP and its specific antibody. A two-site, monoclonal-based immunoassay utilizing monoclonal antibodies reactive to two non-interfering HSQEP epitopes is preferred, but a competitive binding assay may also be employed (Maddox, supra).

In another embodiment of the invention, the polynucleotides encoding HSQEP, or any fragment thereof, or antisense sequences, may be used for therapeutic purposes. In one aspect, antisense to the polynucleotide encoding HSQEP may be used in situations in which it would be desirable to block the synthesis of the protein. In particular, cells may be transformed with sequences complementary to polynucleotides encoding HSQEP. Thus, antisense sequences may be used to modulate HSQEP activity, or to achieve regulation of gene function. Such technology is now well known in the art, and sense or antisense oligomers or larger fragments, can be designed from various locations along the coding or control regions of sequences encoding HSQEP.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense polynucleotides of the gene encoding HSQEP. These techniques are described both in Sambrook et al. (supra) and in Ausubel et al. (supra).

Genes encoding HSQEP can be turned off by transforming a cell or tissue with expression vectors which express high levels of a polynucleotide or fragment thereof which encodes HSQEP. Such constructs may be used to introduce untranslatable sense or antisense sequences into a cell. Even in the absence of integration into the DNA, such vectors may continue to transcribe RNA molecules until all copies are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding HSQEP, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches,* Futura Publishing Co., Mt. Kisco, N.Y.). The antisense molecules may also be designed to block translation of MRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding HSQEP.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding HSQEP. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any suitable subject including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of HSQEP, antibodies to HSQEP, mimetics, agonists, antagonists, or inhibitors of HSQEP. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of HSQEP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example HSQEP or fragments thereof, antibodies of HSQEP, agonists, antagonists or inhibitors of HSQEP, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, ED50/LD50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind HSQEP may be used for the diagnosis of conditions or diseases characterized by expression of HSQEP, or in assays to monitor patients being treated with HSQEP, agonists, antagonists or inhibitors. The antibodies useful for diagnostic purposes may be prepared in the same manner as those described above for therapeutics. Diagnostic assays for HSQEP include methods which utilize the antibody and a label to detect HSQEP in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring HSQEP are known in the art and provide a basis for diagnosing altered or abnormal levels of HSQEP expression. Normal or standard values for HSQEP expression are established by combining body fluids or cell extracts taken from normal mammalian subjects, preferably human, with antibody to HSQEP under conditions suitable for complex formation The amount of standard complex formation may be quantified by various methods, but preferably by photometric, means. Quantities of HSQEP expressed in control and disease samples from biopsied tissues are compared with the standard values. Deviation between standard and subject values establishes the parameters for diagnosing disease.

In another embodiment of the invention, the polynucleotides encoding HSQEP may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of HSQEP may be correlated with disease. The diagnostic assay may be used to distinguish between absence, presence, and excess expression of HSQEP, and to monitor regulation of HSQEP levels during therapeutic intervention.

In one aspect, hybridization with PCR probes which are capable of detecting polynucleotide sequences, including genomic sequences, encoding HSQEP or closely related molecules, may be used to identify nucleic acid sequences which encode HSQEP. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding HSQEP, alleles, or related sequences.

Probes may also be used for the detection of related sequences, and should preferably contain at least 50% of the nucleotides from any of the HSQEP encoding sequences. The hybridization probes of the subject invention may be DNA or RNA and derived from the nucleotide sequence of SEQ ID NO:2 or from genomic sequence including promoter, enhancer elements, and introns of the naturally occurring HSQEP.

Means for producing specific hybridization probes for DNAs encoding HSQEP include the cloning of nucleic acid sequences encoding HSQEP or HSQEP derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding HSQEP may be used for the diagnosis of conditions or diseases which are associated with expression of HSQEP. Examples of such conditions or diseases include disorders of cholesterol metabolism such as hypercholesterolemia. The polynucleotide sequences encoding HSQEP may be used in Southern or northern analysis, dot blot, or other membrane-based technologies; in PCR technologies; or in dip stick, pin, ELISA or chip assays utilizing fluids or tissues from patient biopsies to detect altered HSQEP expression. Such qualitative or quantitative methods are well known in the art.

In a particular aspect, the nucleotide sequences encoding HSQEP may be usefull in assays that detect activation or induction of various cancers, particularly those mentioned above. The nucleotide sequence encoding HSQEP may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequence has hybridized with nucleotide sequences in the sample, and the presence of altered levels of nucleotide sequences encoding HSQEP in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of HSQEP, a normal or standard profile for expression is established. This may be accomplished by combining body fluids or cell extracts taken from normal subjects, either animal or human, with a sequence, or a fragment thereof, which encodes HSQEP, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides encoding HSQEP may involve the use of PCR. Such oligomers may be chemically synthesized, generated enzymatically, or produced from a recombinant source. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of HSQEP include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 212:239–236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequence which encodes HSQEP may also be used to generate hybridization probes which are useful for mapping the naturally occurring genomic sequence. The sequence may be mapped to a particular chromosome or to a specific region of the chromosome using well known techniques . Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma et al. (1988) *Human Chromosomes: A Manual of Basic Techniques,* Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding HSQEP on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, HSQEP, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between HSQEP and the agent being tested, may be measured.

Another technique for drug screening which may be used provides for high throughput screening of compounds having suitable binding affinity to the protein of interest as described in published PCT application WO84/03564. In this method, as applied to HSQEP large numbers of different small test compounds are synthesized on a solid substrate, such as plastic pins or some other surface. The test compounds are reacted with HSQEP, or fragments thereof, and washed. Bound HSQEP is then detected by methods well known in the art. Purified HSQEP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HSQEP specifically compete with a test compound for binding HSQEP. In this manner, the antibodies can be used to detect the presence of any peptide which shares one or more antigenic determinants with HSQEP.

In additional embodiments, the nucleotide sequences which encode HSQEP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

The BRSTNOT03 cDNA library was constructed from tissue removed from the normal breast of a 54 year old female. The frozen tissue was immediately homogenized and lysed using a Brinkmann POLYTRON homogenizer PT-3000 (Brinkmann Instruments Inc, Westbury N.Y.) in guanidinium isothiocyanate solution. Lysates were then loaded on a 5.7M CsCl cushion and ultracentrifuged in a SW28 swinging bucket rotor for 18 hours at 25,000 rpm at ambient temperature. The RNA was extracted once with acid phenol at pH 4.0 and once with phenol chloroform at pH 8.0 and precipitated using 0.3M sodium acetate and 2.5 volumes of ethanol, resuspended in DEPC-treated water and DNase treated for 25 min at 37° C. The reaction was stopped with an equal volume of acid phenol, and the RNA was isolated using the OLIGOTEX kit (Qiagen Inc., Chatsworth, Calif.) and used to construct the cDNA library.

The RNA was handled according to the recommended protocols in the SUPERSCRIPT cDNA SYNTHESIS AND PLAMID CLONING SYSTEM (Cat. No. 18248-013; Gibco/BRL). cDNAs were fractionated on a SEPHAROSE CL4B column (Cat. No. 275105, Pharmacia), and those cDNAs exceeding 400 bp were ligated into the pSPORT 1. The plasmid pSPORT 1 plasmid was subsequently transformed into DH5a competent cells (Cat. No. 18258-012, Gibco/BRL).

II Isolation and Sequencing of cDNA Clones

Plasmid DNA was released from the cells and purified using the MINIPREP KIT (Cat. No. 77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Cat. No. 22711, Life Technologies, Gaithersburg, Md.) with carbenicillin at 25 mg/L and glycerol at 0.4%; 2) the bacteria were cultured for 24 hours after the wells were inoculated and then lysed with 60 µl of lysis buffer; 3) a centrifugation step employing the Beckman GS-6R @2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

The cDNAs were sequenced by the method of Sanger F. and A. R. Coulson (1975; J. Mol. Biol. 94:441f), using a Hamilton MICROLAB 2200 (Hamilton, Reno Nev.) in combination with four Peltier THERMAL CYCLERS (PTC200; MJ Research, Watertown Mass.) and Applied Biosystems 377 or 373 DNA SEQUENCING SYSTEMS (Perkin Elmer), and reading frame was determined.

III Homology Searching of cDNA Clones and Their Deduced Proteins

Each cDNA was compared to sequences in GenBank using a search algorithm developed by Applied Biosystems and incorporated into the INHERIT™ 670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT-670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36:290–300; Altschul et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ® database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\% \text{ sequence identity} \times \% \text{ maximum BLAST score}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding HSQEP occurs. Abundance and percent abundance are also reported. Abundance directly reflects the number of times a particular transcript is represented in a cDNA library, and percent abundance is abundance divided by the total number of sequences examined in the cDNA library.

V Extension of HSQEP-Encoding Polynucleotides to Full Length or to Recover Regulatory Sequences Full length HSQEP-encoding nucleic acid sequence (SEQ ID NO:2) is used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (ELF). Primers are used to facilitate the extension of the known sequence "outward" generating amplicons containing new, unknown nucleotide sequence for the region of interest. The initial primers are designed from the cDNA using OLIGO 4.06 PRIMER ANALYSIS SOFTWARE (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M.J. Research, Watertown, Mass.) and the following parameters:

| Step 1 | 94° C. for 1 min (initial denaturation) |
|---|---|
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQUICK DNA GEL PURIFICATION KIT (QIAGEN Inc., Chatsworth, Calif.). After recovery of the DNA, Klenow enzyme is used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent *E. coli* cells (in 40 μl of appropriate media) are transformed with 3 μl of ligation mixture and cultured in 80 μl of SOC medium (Sambrook et al., supra). After incubation for one hour at 37° C., the whole transformation mixture is plated on Luria Bertani (LB)-agar (Sambrook et al., supra) containing 2× Carb. The following day, several colonies are randomly picked from each plate and cultured in 150 μl of liquid LB/2× Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer, and one or both of the gene specific primers used for the extension reaction are added to each well. Amplification is performed using the following conditions:

| Step 1 | 94° C. for 60 sec |
|---|---|
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of $[\gamma\text{-}^{32}P]$ adenosine triphosphate (Amersham) and T4 polynucleotide kinase (DuPont NEN®, Boston, Mass.). The labeled oligonucleotides are substantially purified with SEPHADEX G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (NYTRAN PLUS membrane, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots or the blots are placed in a Phospho-imager cassette (Molecular Dynamics, Sunnyvale, Calif.) for several hours, hybridization patterns are compared visually.

VII Antisense Molecules

Antisense molecules to the HSQEP-encoding sequence, or any part thereof, is used to inhibit in vivo or in vitro expression of naturally occurring HSQEP. Although use of antisense oligonucleotides, comprising about 20 base-pairs, is specifically described, essentially the same procedure is used with larger cDNA fragments. An oligonucleotide based on the coding sequences of HSQEP, as shown in FIGS. 1A, 1B, and 1C, is used to inhibit expression of naturally occurring HSQEP. The complementary oligonucleotide is designed from the most unique 5' sequence as shown in FIGS. 1A, 1B, and 1C and used either to inhibit transcription by preventing promoter binding to the upstream nontranslated sequence or translation of an HSQEP-encoding transcript by preventing the ribosome from binding. Using an appropriate portion of the signal and 5' sequence of SEQ ID NO:2, an effective antisense oligonucleotide includes any 15–20 nucleotides spanning the region which translates into the signal or 5' coding sequence of the polypeptide as shown in FIGS. 1A, 1B, and 1C.

VIII Expression of HSQEP

Expression of HSQEP is accomplished by subcloning the cDNAs into appropriate vectors and transforming the vectors into host cells. In this case, the cloning vector, pSPORT1, previously used for the generation of the cDNA library is used to express HSQEP in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of HSQEP into the bacterial growth media which can be used directly in the following assay for activity.

IX Demonstration of HSQEP Activity

The HSQEP-catalyzed oxidation of squalene to squalene 2,3-epoxide is assayed as described for rat squalene epoxidase (Sakakibara, J. et al. (1995) J. Biol. Chem. 270:17–20).

Assay mixtures contain HSQEP, 20 mM Tris-HCL pH 7.5, 0.01 mM FAD, 0.2 units of NADPH-cytochrome C (P-450) reductase, 0.01 mM [$^{14}$C]-squalene (dispersed with the aid of 20 µl Tween-80), 0.2% Triton X-100, and 1 mM NADPH in a total volume of 0.5 ml. The reaction is initiated by addition of NADPH. Reaction mixtures are incubated at 37° C. for 30 minutes. Reaction products and [$^{14}$C]-lipid standards are analyzed by silica gel thin-layer chromatography developed in a 0.5/95.5 (v/v) mixture of ethyl acetate/benzene, followed by autoradiography.

X Production of HSQEP Specific Antibodies

HSQEP that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems PEPTIDE SYNTHESIZER MODEL 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring HSQEP Using Specific Antibodies

Naturally occurring or recombinant HSQEP is substantially purified by immunoaffinity chromatography using antibodies specific for HSQEP. An immunoaffinity column is constructed by covalently coupling HSQEP antibody to an activated chromatographic resin, such as CnBr-activated SEPHAROSE RESIN (Pharmacia & Upjohn). After the coupling, the resin is blocked and washed according to the manufacturer's instructions.

Media containing HSQEP is passed over the immunoaffinity column, and the column is washed under conditions that allow the preferential absorbance of HSQEP (e.g., high ionic strength buffers in the presence of detergent). The column is eluted under conditions that disrupt antibody/HSQEP binding (eg, a buffer of pH 2–3 or a high concentration of a chaotrope, such as urea or thiocyanate ion), and HSQEP is collected.

XII Identification of Molecules Which Interact with HSQEP

HSQEP or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled HSQEP, washed and any wells with labeled HSQEP complex are assayed. Data obtained using different concentrations of HSQEP are used to calculate values for the number, affinity, and association of HSQEP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide comprising the nucleic acid sequence of SEQ ID NO:2.

2. An isolated and purified polynucleotide which is complementary to the polynucleotide of claim 1.

3. A hybridization probe comprising the polynucleotide of claim 2.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 572 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY:
        ( B ) CLONE: Consensus ( x i ) SEQUENCE DESCRIPTION: SEQ ID NO:1:

```
Met  Trp  Thr  Phe  Leu  Gly  Ile  Ala  Thr  Phe  Thr  Tyr  Phe  Tyr  Lys  Lys
 1                   5                            10                           15

Phe  Gly  Asp  Phe  Ile  Thr  Leu  Ala  Asn  Arg  Glu  Val  Leu  Leu  Cys  Val
                20                       25                       30

Leu  Val  Phe  Leu  Ser  Leu  Gly  Leu  Val  Leu  Ser  Tyr  Arg  Cys  Arg  His
                35                       40                       45
```

-continued

| | | | | | | | | | | | | | | |
|---|---|---|---|---|---|---|---|---|---|---|---|---|---|---|
| Arg | Asn | Gly | Gly | Leu | Leu | Gly | Arg | Gln | Lys | Ser | Gly | Ser | Gln | Ile | Ala |
| | 50 | | | | | 55 | | | | | 60 | | | | |
| Leu | Phe | Ser | Asp | Ile | Leu | Ser | Gly | Leu | Pro | Phe | Ile | Gly | Phe | Phe | Trp |
| 65 | | | | | 70 | | | | 75 | | | | | | 80 |
| Ala | Asn | Pro | Pro | Leu | Asn | Gln | Lys | Ile | Arg | Ser | Ser | Ser | Arg | Gln | Glu |
| | | | | 85 | | | | | 90 | | | | | 95 | |
| Ala | Gln | Lys | Arg | Asn | Gln | Tyr | Phe | Arg | Asn | Lys | Leu | Asn | Arg | Asn | Ser |
| | | | 100 | | | | | 105 | | | | | 110 | | |
| Cys | Cys | Thr | Ser | Thr | Ser | Ser | Gln | Asn | Asp | Pro | Glu | Val | Ile | Ile | Val |
| | | | 115 | | | | | 120 | | | | | 125 | | |
| Gly | Ala | Gly | Val | Leu | Gly | Ser | Ala | Leu | Ala | Ala | Val | Leu | Ser | Arg | Asp |
| | | 130 | | | | 135 | | | | | 140 | | | | |
| Gly | Arg | Lys | Val | Thr | Val | Ile | Glu | Arg | Asp | Leu | Lys | Glu | Pro | Asp | Arg |
| 145 | | | | | 150 | | | | | 155 | | | | | 160 |
| Ile | Val | Gly | Glu | Phe | Leu | Gln | Pro | Gly | Gly | Tyr | His | Val | Leu | Lys | Asp |
| | | | | 165 | | | | | 170 | | | | | 175 | |
| Leu | Gly | Leu | Gly | Asp | Thr | Val | Glu | Gly | Leu | Asp | Ala | Gln | Val | Val | Asn |
| | | | 180 | | | | | 185 | | | | | 190 | | |
| Gly | Tyr | Met | Ile | His | Asp | Gln | Glu | Ser | Lys | Ser | Glu | Val | Gln | Ile | Pro |
| | | | 195 | | | | 200 | | | | | 205 | | | |
| Asn | Pro | Leu | Ser | Glu | Asn | Gln | Val | Gln | Ser | Gly | Arg | Ala | Phe | His |
| | 210 | | | | | 215 | | | | | 220 | | | | |
| His | Gly | Arg | Phe | Ile | Met | Ser | Leu | Arg | Lys | Ala | Val | Met | Ala | Glu | Pro |
| 225 | | | | | 230 | | | | | 235 | | | | | 240 |
| Asn | Ala | Lys | Phe | Ile | Glu | Gly | Val | Val | Leu | Gln | Leu | Leu | Glu | Glu | Asp |
| | | | | 245 | | | | | 250 | | | | | 255 | |
| Asp | Val | Val | Met | Gly | Val | Gln | His | Lys | Asp | Lys | Glu | Thr | Gly | Asp | Ile |
| | | | 260 | | | | | 265 | | | | | 270 | | |
| Lys | Glu | Leu | His | Ala | Pro | Leu | Thr | Val | Val | Ala | Asp | Gly | Leu | Phe | Ser |
| | | | 275 | | | | 280 | | | | | 285 | | | |
| Lys | Phe | Arg | Lys | Ser | Leu | Val | Ser | Asn | Lys | Val | Ser | Val | Ser | Ser | His |
| | 290 | | | | | 295 | | | | | 300 | | | | |
| Phe | Val | Gly | Phe | Leu | Met | Lys | Asn | Ala | Pro | Gln | Phe | Thr | Ala | Asn | His |
| 305 | | | | | 310 | | | | | 315 | | | | | 320 |
| Ala | Glu | Leu | Ile | Leu | Ala | Asn | Pro | Ser | Pro | Val | Leu | Ile | Tyr | Gln | Ile |
| | | | | 325 | | | | | 330 | | | | | 335 | |
| Ser | Ser | Ser | Glu | Ile | Glu | Tyr | Leu | Leu | Thr | Leu | Glu | Gly | Met | Pro | Arg |
| | | | 340 | | | | | 345 | | | | | 350 | | |
| Asn | Leu | Arg | Glu | Tyr | Met | Val | Glu | Lys | Ile | Tyr | Pro | Gln | Ile | Pro | Asp |
| | | 355 | | | | | 360 | | | | | 365 | | | |
| His | Leu | Lys | Glu | Pro | Phe | Leu | Glu | Ala | Thr | Asp | Asn | Ser | His | Leu | Arg |
| | 370 | | | | | 375 | | | | | 380 | | | | |
| Ser | Met | Pro | Ala | Ser | Phe | Leu | Pro | Pro | Ser | Val | Lys | Lys | Arg | Gly |
| 385 | | | | | 390 | | | | | 395 | | | | | 400 |
| Val | Leu | Leu | Leu | Gly | Asp | Ala | Tyr | Asn | Met | Arg | His | Pro | Leu | Thr | Gly |
| | | | | 405 | | | | | 410 | | | | | 415 | |
| Gly | Gly | Met | Thr | Val | Ala | Phe | Lys | Asp | Ile | Lys | Leu | Trp | Arg | Lys | Leu |
| | | | 420 | | | | | 425 | | | | | 430 | | |
| Leu | Lys | Gly | Ile | Pro | Asp | Leu | Tyr | Asp | Ala | Ala | Ile | Phe | Glu | Ala |
| | | 435 | | | | | 440 | | | | | 445 | | | |
| Lys | Lys | Ser | Phe | Tyr | Trp | Ala | Arg | Lys | Thr | Ser | His | Ser | Phe | Val | Val |
| | 450 | | | | | 455 | | | | | 460 | | | | |
| Asn | Ile | Leu | Ala | Gln | Ala | Leu | Tyr | Glu | Leu | Phe | Ser | Ala | Thr | Asp | Asp |

|  | 465 |  |  |  | 470 |  |  |  | 475 |  |  |  | 480 |  |
|---|---|---|---|---|---|---|---|---|---|---|---|---|---|---|
| Ser | Leu | His | Gln | Leu | Arg | Lys | Ala | Cys | Phe | Leu | Tyr | Phe | Lys | Leu | Gly |
|  |  |  |  | 485 |  |  |  |  | 490 |  |  |  |  | 495 |  |
| Gly | Glu | Cys | Xaa | Ala | Gly | Pro | Val | Gly | Leu | Leu | Ser | Val | Leu | Ser | Pro |
|  |  |  | 500 |  |  |  |  | 505 |  |  |  |  | 510 |  |  |
| Asn | Pro | Leu | Val | Leu | Ile | Gly | His | Phe | Phe | Ala | Val | Ala | Ile | Tyr | Ala |
|  |  | 515 |  |  |  |  | 520 |  |  |  |  | 525 |  |  |  |
| Val | Tyr | Phe | Cys | Phe | Lys | Ser | Glu | Pro | Trp | Ile | Thr | Lys | Pro | Arg | Ala |
|  | 530 |  |  |  |  | 535 |  |  |  |  | 540 |  |  |  |  |
| Leu | Leu | Ser | Ser | Gly | Ala | Val | Leu | Tyr | Lys | Ala | Cys | Ser | Val | Ile | Phe |
| 545 |  |  |  |  | 550 |  |  |  |  | 555 |  |  |  |  | 560 |
| Pro | Leu | Ile | Tyr | Ser | Glu | Met | Lys | Tyr | Met | Val | His |  |  |  |  |
|  |  |  |  | 565 |  |  |  |  | 570 |  |  |  |  |  |  |

( 2 ) INFORMATION FOR SEQ ID NO:2:

( i ) SEQUENCE CHARACTERISTICS:
        ( A ) LENGTH: 2443 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY:
        ( B ) CLONE: Consensus ( x i ) SEQUENCE DESCRIPTION: SEQ ID NO:2:

```
TTCGCCAGCT CCCCGGATTG AAGGTTGCCT GGAGCCGCAC TCTTGAGTCC GAGGCCATCT      60
TTTGTTGGAG AAGGCGTCGG CGTTGGCGTT TTCCCGAGGT TGGGCTGTAC AGTGTCTCCG     120
TCCGCGGAAA AAGAAGCCTC TGAACCCGCG CCGGTCCGCA GCCCCGTGC CTTCCGGACG      180
CTGCTCGCCG TCGCCAGAGG CTAGGCCACG TTTCCCCCAG TGTCGAGGTG TTTCTGCGAC     240
CCTCCCTCCA CTCCCATTCC CTTCTGAAAG GGCACCTGCT CTTGGTGAGA AAAGAAATTA    300
TCGCACGAAG AGCCAGTATC AGAAGAGTAT CCATCACCCG CAGCAACCGC TCAGGGAACA     360
CCATCAAAAA AGAAAAAAAG GGAATATCTG GATTTCCTGG GCGAGGAGGA GCGAGTCTGC     420
TCGGGAGCTG TTCCAGCAGG CGATTTTTAA ATACTGCTTT CTACGCCCTA TACAACTTGG     480
CTTCACATAC TTTTACACTA ACTTTATATG ATTTTAAAA  ACTGGTCTGA TCGGACTTCT    540
CGTCCTGGGA CACTGTTTAC TGGAGTCTGG CCGGCTCTCC GTGCTCCTCT TGGTACCTCA    600
TTTGGGGGAG AACCTTAAAC CCACTCGAGC AGATAATCTC CGCCTTGACC GGTGCCACCA    660
AAGAAGCCTT GGAACCATGT GGACTTTTCT GGGCATTGCC ACTTTCACCT ATTTTTATAA    720
GAAGTTCGGG GACTTCATCA CTTTGGCCAA CAGGGAGGTC CTGTTGTGCG TGCTGGTGTT    780
CCTCTCGCTG GGCCTGGTGC TCTCCTACCG CTGTCGCCAC CGAAACGGGG GTCTCCTCGG    840
GCGCCAGAAG AGCGGCTCCC AGATCGCCCT CTTCTCGGAT ATTCTCTCAG GCCTGCCTTT    900
CATTGGCTTC TTCTGGGCAA ATCCCCCCT  GAATCAGAAA ATAAGGAGCA GCTCGAGGCA    960
GGAGGCGCAG AAAAGGAACC AATATTTCAG AAACAAGCTT AATAGGAACA GCTGCTGTAC   1020
ATCAACATCT TCTCAGAATG ACCCAGAAGT TATCATCGTG GGAGCTGGCG TGCTTGGCTC   1080
TGCTTTGGCA GCTGTGCTTT CCAGAGATGG AAGAAGGTG  ACAGTCATTG AGAGAGACTT   1140
AAAAGAGCCT GACAGAATAG TTGGAGAATT CCTGCAGCCG GGTGGTTATC ATGTTCTCAA   1200
AGACCTTGGT CTTGGAGATA CAGTGGAAGG TCTTGATGCC CAGGTTGTAA ATGGTTACAT   1260
GATTCATGAT CAGGAAAGCA AATCAGAGGT TCAGATTCCT AACCCTCTGT CAGAAAACAA   1320
```

-continued

```
TCAAGTGCAG  AGTGGAAGAG  CTTTCCACCA  CGGAAGATTC  ATCATGAGTC  TCCGGAAAGC   1380
AGTTATGGCA  GAGCCCAATG  CAAAGTTTAT  TGAAGGTGTT  GTGTTACAGT  TATTAGAGGA   1440
AGATGATGTT  GTGATGGGAG  TTCAGCACAA  GGATAAAGAG  ACTGGAGATA  TCAAGGAACT   1500
CCATGCTCCA  CTGACTGTTG  TTGCAGATGG  GCTTTTCTCC  AAGTTCAGGA  AAAGCCTGGT   1560
CTCCAATAAA  GTTTCTGTAT  CATCTCATTT  TGTTGGCTTT  CTTATGAAGA  ATGCACCACA   1620
GTTTACAGCA  AATCATGCTG  AACTTATTTT  AGCTAACCCG  AGTCCAGTTC  TCATCTACCA   1680
GATTTCATCC  AGTGAAATCG  AGTACTTGTT  GACATTAGAG  GGAATGCCAA  GGAATTTAAG   1740
AGAATACATG  GTTGAAAAAA  TTTACCCACA  AATACCTGAT  CACCTGAAAG  AACCATTCTT   1800
AGAAGCCACT  GACAATTCTC  ATCTGAGGTC  CATGCCAGCA  AGCTTCCTTC  CTCCTTCATC   1860
AGTGAAGAAA  CGAGGTGTTC  TTCTTTTGGG  AGACGCATAT  AATATGAGGC  ATCCACTTAC   1920
TGGTGGAGGA  ATGACTGTTG  CTTTTAAAGA  TATAAAACTA  TGGAGAAAAC  TGCTAAAGGG   1980
TATCCCTGAC  CTTTATGATG  ATGCAGCTAT  TTTCGAGGCC  AAAAAATCAT  TTTACTGGGC   2040
AAGAAAAACA  TCTCATTCCT  TTGTCGTGAA  TATCCTTGCT  CAGGCTCTTT  ATGAATTATT   2100
TTCTGCCACA  GATGATTCCC  TGCATCAACT  AAGAAAAGCC  TGTTTTCTTT  ATTTCAAACT   2160
TGGTGGCGAA  TGTNTTGCGG  GTCCTGTTGG  GCTGCTTTCT  GTATTGTCTC  CTAACCCTCT   2220
AGTTTTAATT  GGACACTTCT  TTGCTGTTGC  AATCTATGCC  GTGTATTTTT  GCTTTAAGTC   2280
AGAACCTTGG  ATTACAAAAC  CTCGAGCCCT  TCTCAGTAGT  GGTGCTGTAT  TGTACAAAGC   2340
GTGTTCTGTA  ATATTTCCTC  TAATTTACTC  AGAAATGAAG  TATATGGTTC  ATTAAGCTTA   2400
AAGGGGAACC  ATTTGTGAAT  GAATATTTGG  AACTTACCAA  GTC                      2443
```

( 2 ) INFORMATION FOR SEQ ID NO:3:

( i ) SEQUENCE CHARACTERISTICS:
        ( A ) LENGTH: 572 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: 1217593

( x i ) SEQUENCE DESCRIPTION: SEQ ID NO:3:

```
Met  Trp  Thr  Phe  Leu  Gly  Ile  Ala  Thr  Phe  Thr  Tyr  Phe  Tyr  Lys  Lys
 1              5                        10                       15

Cys  Gly  Asp  Val  Thr  Leu  Ala  Asn  Lys  Glu  Leu  Leu  Leu  Cys  Val  Leu
              20                        25                       30

Val  Phe  Leu  Ser  Leu  Gly  Leu  Val  Leu  Ser  Tyr  Arg  Cys  Arg  His  Arg
              35                        40                       45

His  Gly  Gly  Leu  Leu  Gly  Arg  His  Gln  Ser  Gly  Ala  Gln  Phe  Ala  Ala
              50                        55                       60

Phe  Ser  Asp  Ile  Leu  Ser  Ala  Leu  Pro  Leu  Ile  Gly  Phe  Phe  Trp  Ala
 65                       70                       75                       80

Lys  Ser  Pro  Glu  Ser  Glu  Lys  Lys  Glu  Gln  Leu  Glu  Ser  Lys  Lys  Cys
                         85                       90                       95

Arg  Lys  Glu  Ile  Gly  Leu  Ser  Glu  Thr  Thr  Leu  Thr  Gly  Ala  Ala  Thr
                        100                      105                      110

Ser  Val  Ser  Thr  Ser  Phe  Val  Thr  Asp  Pro  Glu  Val  Ile  Ile  Val  Gly
                        115                      120                      125
```

| Ser | Gly | Val | Leu | Gly | Ser | Ala | Leu | Ala | Ala | Val | Leu | Ser | Arg | Asp | Gly |
|-----|-----|-----|-----|-----|-----|-----|-----|-----|-----|-----|-----|-----|-----|-----|-----|
|     | 130 |     |     |     | 135 |     |     |     |     | 140 |     |     |     |     |     |

| Arg | Lys | Val | Thr | Val | Ile | Glu | Arg | Asp | Leu | Lys | Glu | Pro | Asp | Arg | Ile |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Val | Gly | Glu | Leu | Gln | Pro | Gly | Gly | Tyr | Arg | Val | Leu | Gln | Glu | Leu |
|-----|-----|-----|-----|-----|-----|-----|-----|-----|-----|-----|-----|-----|-----|-----|
|     |     |     |     | 165 |     |     |     |     | 170 |     |     |     | 175 |     |

| Gly | Leu | Gly | Asp | Thr | Val | Glu | Gly | Leu | Asn | Ala | His | His | Ile | His | Gly |
|-----|-----|-----|-----|-----|-----|-----|-----|-----|-----|-----|-----|-----|-----|-----|-----|
|     |     |     | 180 |     |     |     |     | 185 |     |     |     |     |     | 190 |     |

| Tyr | Ile | Val | His | Asp | Tyr | Glu | Ser | Arg | Ser | Glu | Val | Gln | Ile | Pro | Tyr |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Pro | Leu | Ser | Glu | Thr | Asn | Gln | Val | Gln | Ser | Gly | Ile | Ala | Phe | His | His |
|-----|-----|-----|-----|-----|-----|-----|-----|-----|-----|-----|-----|-----|-----|-----|-----|
|     |     | 210 |     |     |     |     | 215 |     |     |     |     | 220 |     |     |     |

| Gly | Arg | Phe | Ile | Met | Ser | Leu | Arg | Lys | Ala | Ala | Met | Ala | Glu | Pro | Asn |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Val | Lys | Phe | Ile | Glu | Gly | Val | Val | Leu | Gln | Leu | Leu | Glu | Glu | Asp | Asp |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Ala | Val | Ile | Gly | Val | Gln | Tyr | Lys | Asp | Lys | Glu | Thr | Gly | Asp | Thr | Lys |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Glu | Leu | His | Ala | Pro | Leu | Thr | Val | Ala | Asp | Gly | Leu | Phe | Ser | Lys |
|-----|-----|-----|-----|-----|-----|-----|-----|-----|-----|-----|-----|-----|-----|-----|
|     |     | 275 |     |     |     |     | 280 |     |     |     | 285 |     |     |     |

| Phe | Arg | Lys | Ser | Leu | Ile | Ser | Ser | Lys | Val | Ser | Val | Ser | Ser | His | Phe |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Val | Gly | Phe | Leu | Met | Lys | Asp | Ala | Pro | Gln | Phe | Lys | Pro | Asn | Phe | Ala |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Glu | Leu | Val | Leu | Val | Asn | Pro | Ser | Pro | Val | Leu | Ile | Tyr | Gln | Ile | Ser |
|-----|-----|-----|-----|-----|-----|-----|-----|-----|-----|-----|-----|-----|-----|-----|-----|
|     |     |     |     | 325 |     |     |     |     | 330 |     |     |     |     | 335 |     |

| Ser | Ser | Glu | Thr | Arg | Val | Leu | Val | Asp | Ile | Arg | Gly | Glu | Leu | Pro | Arg |
|-----|-----|-----|-----|-----|-----|-----|-----|-----|-----|-----|-----|-----|-----|-----|-----|
|     |     |     | 340 |     |     |     |     | 345 |     |     |     |     | 350 |     |     |

| Asn | Leu | Arg | Glu | Tyr | Met | Ala | Glu | Gln | Ile | Tyr | Pro | Gln | Leu | Pro | Glu |
|-----|-----|-----|-----|-----|-----|-----|-----|-----|-----|-----|-----|-----|-----|-----|-----|
|     |     | 355 |     |     |     |     | 360 |     |     |     |     | 365 |     |     |     |

| His | Leu | Lys | Glu | Ser | Phe | Leu | Glu | Ala | Ser | Gln | Asn | Gly | Arg | Leu | Arg |
|-----|-----|-----|-----|-----|-----|-----|-----|-----|-----|-----|-----|-----|-----|-----|-----|
|     |     | 370 |     |     |     |     | 375 |     |     |     |     | 380 |     |     |     |

| Thr | Met | Pro | Ala | Ser | Phe | Leu | Pro | Pro | Ser | Ser | Val | Asn | Lys | Arg | Gly |
|-----|-----|-----|-----|-----|-----|-----|-----|-----|-----|-----|-----|-----|-----|-----|-----|
| 385 |     |     |     |     | 390 |     |     |     |     | 395 |     |     |     |     | 400 |

| Val | Leu | Ile | Leu | Gly | Asp | Ala | Tyr | Asn | Leu | Arg | His | Pro | Leu | Thr | Gly |
|-----|-----|-----|-----|-----|-----|-----|-----|-----|-----|-----|-----|-----|-----|-----|-----|
|     |     |     |     | 405 |     |     |     |     | 410 |     |     |     |     | 415 |     |

| Gly | Gly | Met | Thr | Val | Ala | Leu | Lys | Asp | Ile | Lys | Leu | Trp | Arg | Gln | Leu |
|-----|-----|-----|-----|-----|-----|-----|-----|-----|-----|-----|-----|-----|-----|-----|-----|
|     |     |     | 420 |     |     |     |     | 425 |     |     |     |     | 430 |     |     |

| Leu | Lys | Asp | Ile | Pro | Asp | Leu | Tyr | Asp | Asp | Ala | Ala | Ile | Phe | Gln | Ala |
|-----|-----|-----|-----|-----|-----|-----|-----|-----|-----|-----|-----|-----|-----|-----|-----|
|     |     | 435 |     |     |     |     | 440 |     |     |     |     | 445 |     |     |     |

| Lys | Lys | Ser | Phe | Phe | Trp | Ser | Arg | Lys | Arg | Thr | His | Ser | Phe | Val | Val |
|-----|-----|-----|-----|-----|-----|-----|-----|-----|-----|-----|-----|-----|-----|-----|-----|
|     | 450 |     |     |     |     | 455 |     |     |     |     | 460 |     |     |     |     |

| Asn | Val | Leu | Ala | Gln | Ala | Leu | Tyr | Glu | Leu | Phe | Ser | Ala | Thr | Asp | Asp |
|-----|-----|-----|-----|-----|-----|-----|-----|-----|-----|-----|-----|-----|-----|-----|-----|
| 465 |     |     |     |     | 470 |     |     |     |     | 475 |     |     |     |     | 480 |

| Ser | Leu | His | Gln | Leu | Arg | Lys | Ala | Cys | Phe | Leu | Tyr | Phe | Lys | Leu | Gly |
|-----|-----|-----|-----|-----|-----|-----|-----|-----|-----|-----|-----|-----|-----|-----|-----|
|     |     |     |     | 485 |     |     |     |     | 490 |     |     |     |     | 495 |     |

| Gly | Glu | Cys | Val | Thr | Gly | Pro | Val | Gly | Leu | Leu | Ser | Ile | Leu | Ser | Pro |
|-----|-----|-----|-----|-----|-----|-----|-----|-----|-----|-----|-----|-----|-----|-----|-----|
|     |     |     | 500 |     |     |     |     | 505 |     |     |     |     | 510 |     |     |

| His | Pro | Leu | Val | Leu | Ile | Arg | His | Phe | Phe | Ser | Val | Ala | Ile | Tyr | Ala |
|-----|-----|-----|-----|-----|-----|-----|-----|-----|-----|-----|-----|-----|-----|-----|-----|
|     |     |     | 515 |     |     |     |     | 520 |     |     |     |     | 525 |     |     |

| Thr | Tyr | Phe | Cys | Phe | Lys | Ser | Glu | Pro | Trp | Ala | Thr | Lys | Pro | Arg | Ala |
|-----|-----|-----|-----|-----|-----|-----|-----|-----|-----|-----|-----|-----|-----|-----|-----|
|     |     | 530 |     |     |     |     | 535 |     |     |     |     | 540 |     |     |     |

| Leu | Phe | Ser | Ser | Gly | Ala | Val | Leu | Tyr | Lys | Ala | Cys | Ser | Ile | Leu | Phe |
|-----|-----|-----|-----|-----|-----|-----|-----|-----|-----|-----|-----|-----|-----|-----|-----|
| 545 |     |     |     |     | 550 |     |     |     |     | 555 |     |     |     |     | 560 |

Pro Leu Ile Tyr Ser Glu Met Lys Tyr Leu Val His
565                          570

(2) INFORMATION FOR SEQ ID NO:4:

(i) SEQUENCE CHARACTERISTICS:
      (A) LENGTH: 573 amino acids
      (B) TYPE: amino acid
      (C) STRANDEDNESS: single
      (D) TOPOLOGY: linear (ii) MOLECULE TYPE: peptide (vii) IMMEDIATE SOURCE:
      (A) LIBRARY: GenBank
      (B) CLONE: 1083804

(xi) SEQUENCE DESCRIPTION: SEQ ID NO:4:

Met Trp Thr Phe Leu Gly Ile Ala Thr Phe Thr Tyr Phe Tyr Lys Lys
1               5                   10                  15

Cys Gly Asp Val Thr Leu Ala Asn Lys Glu Leu Leu Leu Cys Val Leu
                20                  25                  30

Val Phe Leu Ser Leu Gly Leu Val Leu Ser Tyr Arg Cys Arg His Arg
            35                  40                  45

Asn Gly Gly Leu Leu Gly Arg His Gln Ser Gly Ser Gln Phe Ala Ala
        50                  55                  60

Phe Ser Asp Ile Leu Ser Ala Leu Pro Leu Ile Gly Phe Phe Trp Ala
65                  70                  75                  80

Lys Ser Pro Pro Glu Ser Lys Lys Glu Gln Leu Glu Ser Lys Arg
                85                  90                  95

Arg Arg Lys Glu Val Asn Leu Ser Glu Thr Thr Leu Thr Gly Ala Ala
            100                 105                 110

Thr Ser Val Ser Thr Ser Ser Val Thr Asp Pro Glu Val Ile Ile Ile
            115                 120                 125

Gly Ser Gly Val Leu Gly Ser Ala Leu Ala Thr Val Leu Ser Arg Asp
        130                 135                 140

Gly Arg Thr Val Thr Val Ile Glu Arg Asp Leu Lys Glu Pro Asp Arg
145                 150                 155                 160

Ile Leu Gly Glu Cys Leu Gln Pro Gly Gly Tyr Arg Val Leu Arg Glu
                165                 170                 175

Leu Gly Leu Gly Asp Thr Val Glu Ser Leu Asn Ala His His Ile His
            180                 185                 190

Gly Tyr Val Ile His Asp Cys Glu Ser Arg Ser Glu Val Gln Ile Pro
        195                 200                 205

Tyr Pro Val Ser Glu Asn Asn Gln Val Gln Ser Gly Val Ala Phe His
    210                 215                 220

His Gly Lys Phe Ile Met Ser Leu Arg Lys Ala Ala Met Ala Glu Pro
225                 230                 235                 240

Asn Val Lys Phe Ile Glu Gly Val Val Leu Arg Leu Leu Glu Glu Asp
                245                 250                 255

Asp Ala Val Ile Gly Val Gln Tyr Lys Asp Lys Glu Thr Gly Asp Thr
            260                 265                 270

Lys Glu Leu His Ala Pro Leu Thr Val Val Ala Asp Gly Leu Phe Ser
        275                 280                 285

Lys Phe Arg Lys Asn Leu Ile Ser Asn Lys Val Ser Val Ser Ser His
    290                 295                 300

Phe Val Gly Phe Ile Met Lys Asp Ala Pro Gln Phe Lys Ala Asn Phe
305                 310                 315                 320

```
Ala Glu Leu Val Leu Val Asp Pro Ser Pro Val Leu Ile Tyr Gln Ile
                325                 330                 335
Ser Pro Ser Glu Thr Arg Val Leu Val Asp Ile Arg Gly Glu Leu Pro
            340                 345                 350
Arg Asn Leu Arg Glu Tyr Met Thr Glu Gln Ile Tyr Pro Gln Ile Pro
        355                 360                 365
Asp His Leu Lys Glu Ser Phe Leu Glu Ala Cys Gln Asn Ala Arg Leu
    370                 375                 380
Arg Thr Met Pro Ala Ser Phe Leu Pro Pro Ser Ser Val Asn Lys Arg
385                 390                 395                 400
Gly Val Leu Leu Leu Gly Asp Ala Tyr Asn Leu Arg His Pro Leu Thr
                405                 410                 415
Gly Gly Gly Met Thr Val Ala Leu Lys Asp Ile Lys Ile Trp Arg Gln
            420                 425                 430
Leu Leu Lys Asp Ile Pro Asp Leu Tyr Asp Asp Ala Ala Ile Phe Gln
        435                 440                 445
Ala Lys Lys Ser Phe Phe Trp Ser Arg Lys Arg Ser His Ser Phe Val
    450                 455                 460
Val Asn Val Leu Ala Gln Ala Leu Tyr Glu Leu Phe Ser Ala Thr Asp
465                 470                 475                 480
Asp Ser Leu Arg Gln Leu Arg Lys Ala Cys Phe Leu Tyr Phe Lys Leu
                485                 490                 495
Gly Gly Glu Cys Leu Thr Gly Pro Val Gly Leu Leu Ser Ile Leu Ser
            500                 505                 510
Pro Asp Pro Leu Leu Leu Ile Arg His Phe Phe Ser Val Ala Val Tyr
        515                 520                 525
Ala Thr Tyr Phe Cys Phe Lys Ser Glu Pro Trp Ala Thr Lys Pro Arg
    530                 535                 540
Ala Leu Phe Ser Ser Gly Ala Ile Leu Tyr Lys Ala Cys Ser Ile Ile
545                 550                 555                 560
Phe Pro Leu Ile Tyr Ser Glu Met Lys Tyr Leu Val His
                565                 570
```